(12) United States Patent
Franz et al.

(10) Patent No.: US 9,844,661 B2
(45) Date of Patent: Dec. 19, 2017

(54) COMPLIANT ELECTRICAL STIMULATION LEADS AND METHODS OF FABRICATION

(75) Inventors: Brian Franz, Flower Mound, TX (US); John Swanson, Portland, OR (US); Jerome Boogaard, Forest Grove, OR (US); Terry D. Daglow, Allen, TX (US); Tom Sosebee, Allen, TX (US); Stephen L. Goldman, Frisco, TX (US); Rajasree (Sarah) Das, Dallas, TX (US); Michael DiGiacomo, Portland, OR (US)

(73) Assignee: Advanced Neuromodulation Systems Inc., Plano, TX (US)

( * ) Notice: Subject to any disclaimer, the term of this patent is extended or adjusted under 35 U.S.C. 154(b) by 1130 days.

(21) Appl. No.: 13/352,785

(22) Filed: Jan. 18, 2012

(65) Prior Publication Data
US 2012/0110846 A1    May 10, 2012

Related U.S. Application Data

(62) Division of application No. 11/694,563, filed on Mar. 30, 2007, now abandoned.

(60) Provisional application No. 60/788,518, filed on Mar. 31, 2006.

(51) Int. Cl.
*A61N 1/00* (2006.01)
*A61N 1/05* (2006.01)

(52) U.S. Cl.
CPC .......... *A61N 1/0551* (2013.01); *A61N 1/0504* (2013.01); *A61N 1/0558* (2013.01); *Y10T 29/49208* (2015.01)

(58) Field of Classification Search
None
See application file for complete search history.

(56) References Cited

U.S. PATENT DOCUMENTS

| | | |
|---|---|---|
| 2,139,055 A | 12/1938 | Wright |
| 4,559,951 A | 12/1985 | Dahl et al. |
| 5,138,138 A | 8/1992 | Theilacker et al. |

(Continued)

FOREIGN PATENT DOCUMENTS

EP    0408358 A2    1/1991

OTHER PUBLICATIONS

ISA/US, Commissioner for Patents, International Search Report for PCT/US07/65677 dated Jan. 29, 2008.

(Continued)

*Primary Examiner* — Christopher D Koharski
*Assistant Examiner* — Elizabeth K So

(57) ABSTRACT

In one embodiment, a neurostimulation lead for stimulating neural tissue of a patient, comprises: a lead body of insulative material; a plurality of electrodes; a plurality of terminals; a plurality of conductors, wherein the plurality of electrodes are electrically coupled to the plurality of terminals through the plurality of conductors; wherein the plurality of conductors are disposed in a helical manner in a repeating pattern of groups of conductors separated by gaps along a substantial length of the lead body, each gap being larger than an inter-conductor pitch within the groups of conductors; wherein the insulative material is a compliant material permitting elongation of the lead at low stretching forces and the insulative material of the lead body is fused through a substantial volume of the lead body and along a substantial length of the lead body.

9 Claims, 5 Drawing Sheets

(56) References Cited

U.S. PATENT DOCUMENTS

| | | |
|---|---|---|
| 5,378,234 A | 1/1995 | Hammerslag |
| 5,417,208 A | 5/1995 | Winkler |
| 5,466,253 A | 11/1995 | Doan |
| 6,208,881 B1 | 3/2001 | Champeau |
| 6,477,427 B1 | 11/2002 | Stolz et al. |
| 6,480,747 B2 | 11/2002 | Schmidt |
| 7,031,777 B2 | 4/2006 | Hine et al. |
| 7,146,222 B2 | 12/2006 | Boling |
| 7,555,349 B2 | 6/2009 | Wessman et al. |
| 7,672,736 B2 | 3/2010 | Boling |
| 2002/0143377 A1 | 10/2002 | Wessman et al. |
| 2003/0060868 A1 | 3/2003 | Janke et al. |
| 2003/0236562 A1 | 12/2003 | Kuzma |
| 2004/0064173 A1 | 4/2004 | Hine et al. |
| 2005/0027338 A1 | 2/2005 | Hill |
| 2005/0027339 A1 | 2/2005 | Schrom et al. |
| 2005/0027340 A1 | 2/2005 | Schrom et al. |
| 2005/0027341 A1 | 2/2005 | Schrom et al. |
| 2005/0288761 A1 | 12/2005 | Brabec et al. |
| 2006/0041295 A1 | 2/2006 | Osypka |
| 2006/0089691 A1 | 4/2006 | Kaplan et al. |
| 2006/0089695 A1 | 4/2006 | Bolea et al. |
| 2006/0089697 A1 | 4/2006 | Cross, Jr. et al. |
| 2006/0111768 A1 | 5/2006 | Wessman et al. |
| 2006/0241734 A1 | 10/2006 | Marshall et al. |

OTHER PUBLICATIONS

European Patent Office, Supplementary European Search Report for EP07759864 dated Nov. 19, 2012.

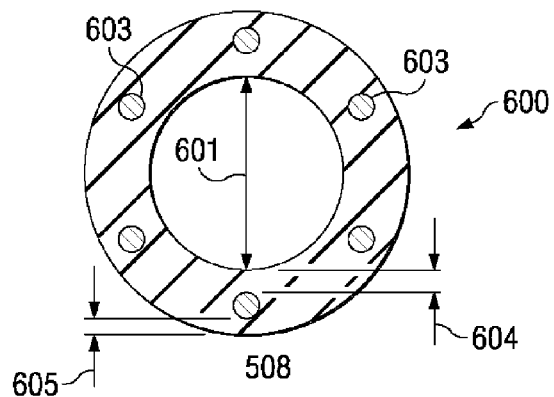
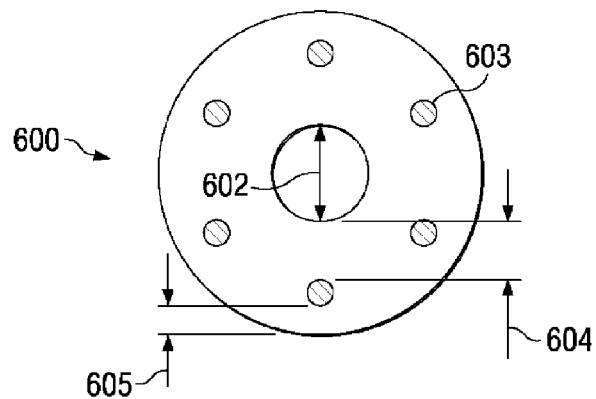
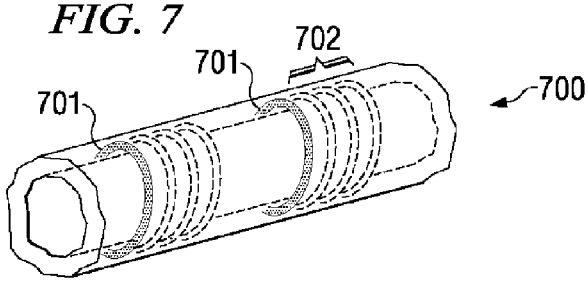
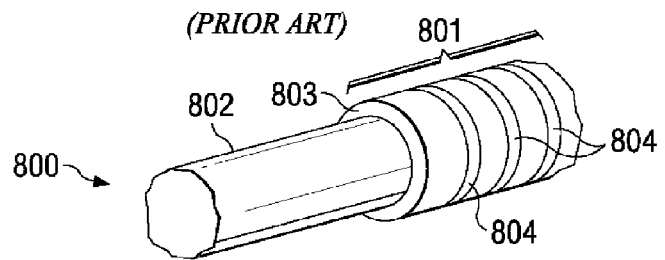

COMPLIANT ELECTRICAL STIMULATION LEADS AND METHODS OF FABRICATION

RELATED APPLICATIONS

This application is a divisional of U.S. application Ser. No. 11/694,563, filed Mar. 30, 2007, pending, which claims the benefit of U.S. Provisional Application No. 60/788,518, filed Mar. 31, 2006, the disclosures of which are fully incorporated herein by reference.

TECHNICAL FIELD

This application is generally related to electrical stimulation leads and methods of their manufacture.

BACKGROUND

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. Other examples include deep brain stimulation, cortical stimulation, cochlear nerve stimulation, peripheral nerve stimulation, vagal nerve stimulation, sacral nerve stimulation, etc. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or more leads. The pulse generator is typically implemented using a metallic housing that encloses circuitry for generating the electrical pulses, control circuitry, communication circuitry, a rechargeable battery, etc. The pulse generation circuitry is coupled to one or more stimulation leads through electrical connections provided in a "header" of the pulse generator. Stimulation leads typically include multiple wire conductors enclosed or embedded within a lead body of insulative material. Terminals and electrodes are located on the proximal and distal ends of the leads. The conductors of the leads electrically couple the terminals to the electrodes. The electrical pulses from the pulse generator are conducted through the leads and applied to patient tissue by the electrodes of the leads.

SUMMARY

In one embodiment, a neurostimulation lead for stimulating neural tissue of a patient, comprises: a lead body of insulative material; a plurality of electrodes; a plurality of terminals; a plurality of conductors, wherein the plurality of electrodes are electrically coupled to the plurality of terminals through the plurality of conductors; wherein the plurality of conductors are disposed in a helical manner in a repeating pattern of groups of conductors separated by gaps along a substantial length of the lead body, each gap being larger than an inter-conductor pitch within the groups of conductors; wherein the insulative material is a compliant material permitting elongation of the lead at low stretching forces and the insulative material of the lead body is fused through a substantial volume of the lead body and along a substantial length of the lead body.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIGS. 6a and 6b show diagrams of conductor positional control in leads manufactured according to some representative embodiments.

FIG. 7 shows a lead according to an embodiment that has conductors marked for identification.

FIG. 8 shows a lead comprising electrodes bonded according to one representative embodiment.

DETAILED DESCRIPTION

Figure 1A:
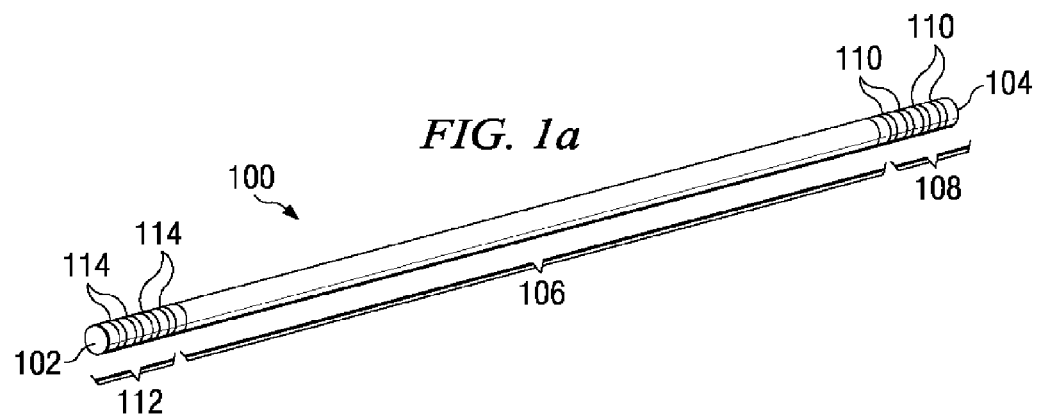
FIGS. 1a and 1b show leads according to some representative embodiments.

Referring now to the drawings, FIG. 1a shows a lead according to one representative embodiment. Lead 100 comprises distal end 102 and proximal end 104. Lead 100 further comprises lead body 106 that extends from distal end 102 to proximal end 104. Adjacent to distal end 102 of lead 100 is stimulation electrode region 108 comprising, in this embodiment, four stimulation electrodes 110. Stimulation electrodes 110 are generally placed in proximity to a stimulation site within a patient's body that is to receive electrical stimulation.

Adjacent to proximal end 104 of lead 100 is connector region 112 that comprises four connector electrodes 114. Connector electrodes 114 are generally in electrical contact with a medical device (not shown) used to generate electrical signals that are applied to connector electrodes 114. In certain embodiments, connector electrodes 114 deliver electrical signals to an attached medical device from electrodes present at distal end 102. Both stimulation electrodes 110 and connector electrodes 114 are generally formed of biocompatible, conductive materials such as stainless steel, platinum, MP35N, biocompatible alloys, etc. Stimulation electrodes 110 and connector electrodes 114 may encircle portions of the stimulation region 108 and connector region 112, respectively, and are connected to one or more conductors of the lead body. Certain embodiments may use electrodes described in co-pending U.S. patent application Ser. No. 11/143,160, filed Jun. 2, 2005 entitled "Notched Electrode for Electrostimulation Lead," the contents of which are herein incorporated by reference in the entirety.

Lead 100 generally includes one or more conductors (not shown) extending along a substantial portion of lead 100 to electrically connect connector electrodes 114 to respective stimulation electrodes 110. Conductors are generally formed of a conductive material having desirable characteristics such as biocompatibility, corrosion resistance, flexibility, strength, low resistance, etc. Lead body conductors may take the form of solid wires, drawn-filled-tube (DFT), drawn-brazed-strand (DBS), stranded wires or cables, ribbon conductors, or other forms known or recognized to those skilled in the art. The composition of the conductors may include aluminum, stainless steel, MP35N, platinum, gold, silver, copper, vanadium, alloys, or other conductive materials or metals known to those of ordinary skill in the art. The number, size, and composition of the conductors will depend on the particular application for lead 100, as well as the number of electrodes.

Lead body conductors of various embodiments are preferably helically wound within the fused insulative material of lead body 106. The helical winding of the conductors is preferably controlled to permit elongation of lead 100 at relatively low stretching forces as further discussed below. Lead body 106 may optionally include a lumen to accommodate a stylet to facilitate implantation of the lead 100 within a patient. The conductors of lead 100 are maintained in electrical isolation by the insulative material of lead body 106. Application of extruded insulative materials are described in co-pending U.S. patent application Ser. No. 10/630,376 filed Jul. 29, 2003, entitled "System and Method for Providing A Medical Lead Body Having Conductors That Are Wound in Opposite Directions," and U.S. patent application Ser. No. 10/630,233 filed Jul. 29, 2003, entitled "System and Method for Providing A Medical Lead Body Having Dual Conductor Layers," the contents of which are herein incorporated by reference in their entirety. In these applications, insulative material of the lead body is individually applied over the wire conductors. The wire conductors are wound about one or more insulative layers and one or more outer insulative layers are extruded over the conductors and inner insulative layer(s). The assembly is then subjected to heat and pressure (e.g., using shrink-wrap tubing) to fuse the insulative material into a solid, fused lead body having the conductors embedded therein. Variations in the insulative material are comtemplated. For example, different insulative materials may be employed for different layers. Also, a relatively hard, thin insulative layer may be initially applied to coat the wire conductors and another insulative layer of lower durometer, more compliant material applied to the conductors.

In a preferred embodiment, lead 100 is generally configured to transmit one or more electrical signals from a stimulation source for application at, or proximate to, a spinal nerve or peripheral nerve, or other tissue. In certain embodiments, an optional lumen (not shown) may extend through lead 100 and may be used for different purposes, such as for stiffening stylettes, delivery of medications or other fluids, etc.

For purposes of illustration only, lead 100 of FIG. 1a is shown with four electrodes. As will be appreciated, any number of conductors and electrodes may be utilized as desired to form lead 100. Generally, some embodiments have the same number of stimulation electrodes as connector electrodes. Other types, configurations and shapes of electrodes as known to those skilled in the art may be used with embodiments. Lead stimulation electrodes 110 and/or connector electrodes 114 are typically made of a conductive material such as platinum, gold, silver, platinum-iridium, stainless steel, MS35N, or other conductive materials, metals or alloys known to those skilled in the art. The size of the electrodes is generally chosen based upon the desired application.

Typically, lead body 106 is a structure having a round or substantially round cross-section. Alternatively, the cross-section of lead body 106 may be configured in any number of cross-sectional shapes appropriate for a specific application in which lead 100 will be used. Lead body 106 generally includes a lead body insulator configured to insulate the conductors and present a biocompatible external surface to the body tissue.

Lead body 106 insulator is formed of insulating material typically selected based upon biocompatibility, biostability and durability for the particular application. The insulator material may be silicone, polyurethane, polyethylene, polyamide, polyvinylchloride, PTFT, EFTE, or other suitable materials known to those skilled in the art. Alloys or blends of these materials may also be formulated to control the relative flexibility, torqueability, and pushability of lead 100. In preferred embodiments, the insulative material of lead body 106 is substantially composed of a compliant PUR-SIL® or CARBOSIL® silicone-urethane copolymer material. The compliant material characteristic enables lead body 106 to elongate significant amounts at relatively low stretching forces. Depending on the particular application, the diameter of the lead body 106 may be any size, though a smaller size is more desirable for lead applications such as neurological and myocardial mapping/ablation and neuromodulation and stimulation.

Figure 1B:
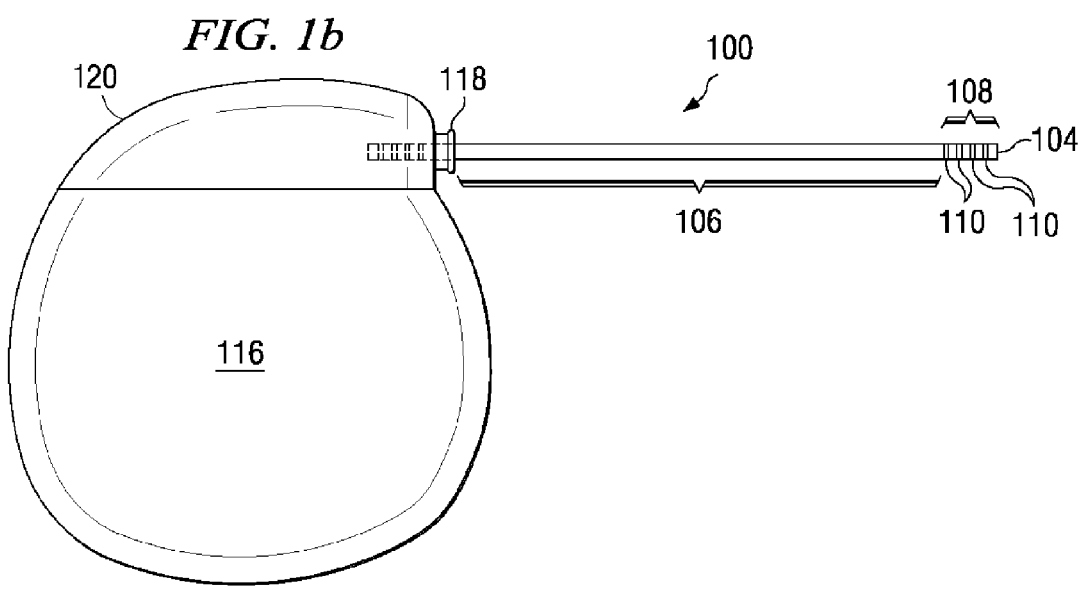

FIG. 1b shows a medical device for generating and applying an electrical signal via a lead according to an embodiment. Lead 100 is connected to pulse generator 116 via receptacle 118. Connector terminals 114 are in electrical contact with electrical connectors (not shown) within header 120. Feedthrough wires (not shown) connect the electrical connectors to pulse generating circuitry (not shown) within pulse generator 116. Pulse generator 116 applies electrical signals to terminals 114 that are themselves in electrical contact with stimulation electrodes 110 at distal end of lead 100. Conductors (not shown) that run along length of lead body 106 electrically connect terminals 114 with stimulation electrodes 110. Lead 100 may be detached from pulse generator 116 as desired by applying detaching force and removing proximal end 102 from header 120. Pulse generator 116 preferably allows variation of stimulation parameters such as frequency, voltage, duration, etc. of applied electrical signals by communication with an external programming device (not shown) in certain embodiments. An example of a commercially available pulse generator that may be used with leads according to some representative embodiments is the EON® pulse generator available from Advanced Neuromodulation Systems, Inc.

In some representative embodiments, an implantable stimulation lead is adapted to accommodate a relatively large amount of stretching after implantation within a patient. For example, in some studies, it has been observed that an implantable lead used for certain spinal cord stimulation can experience nine inches of stretching for an individual that has a height of six feet in response to changes in the person's posture. Conventionally, "service" loops are provided to accommodate the necessity of providing additional length when a patient changes their posture to prevent dislocation of the lead and/or detachment of the lead from the pulse generator. In contrast, some representative embodiments enable the additional length to be obtained from elongation of the lead as an alternative to or in addition to service loops. Additionally, some representative embodiments enable the additional length to be obtained by relatively low stretching forces thereby avoiding dislocation of the lead and/or detachment from the pulse generator.

In one embodiment, an implantable stimulation lead for delivering electrical stimulation to tissue of a patient comprises a lead body of insulative material; a plurality of conductors helically wound within the lead body; and a plurality of electrodes disposed on a distal end of the lead body with each electrode coupled to at least one of the plurality of conductors; wherein the physical characteristics of the plurality of conductors and the lead body allow the lead body to stretch and the conductors to elongate at least 25% when a stretching force of less than 3 lbs is experienced by the lead body.

In some embodiments, the lead body stretches nine inches or more when a force of less than 3 lbs is experienced by the lead body. In some embodiments, the unstretched length of the lead body is approximately 24 inches to accommodate the potential stretching ranges for a large population of patients. The range of force to obtain the desired stretching can be varied by appropriate selection of polymer characteristics, lead conductor characteristics, and manufacturing techniques. The range of force can include stretching forces from 1 to 5 pounds in some embodiments. Additionally, the range of stretching can also vary anywhere from 15%, 25%, 35%, to 40% according to some embodiments.

In addition or in place of the features described above, systems and methods according to some embodiments may use one or more of the additional lead features disclosed below.

I. Stranded Conductor Leads

Conventional medical device leads often use unstranded or solid conductors. While stranded and unstranded conductors of similar size and composition have approximately the same conductivity, unstranded conductors do not possess the fatigue resistance of stranded conductors. Furthermore, stranded conductors can be coiled for additional fatigue resistance.

Stranded conductors aid in the placement of device leads. For example, in certain medical applications, a lead must be implanted in a patient using a certain amount of force. Often the force used results in the lead bending. If a lead comprising unstranded conductors is used, often only a few bends result in breakage of the unstranded conductors. Conductor breakage is prevented in certain embodiments by manufacturing a lead comprising stranded conductors that are helically wound around one or several inner insulative layers. In some embodiments, a lumen is formed within the inner insulative layer. A stiffening stylette can then be inserted in the central lumen, and the stranded lead/stylette assembly inserted, thus avoiding breakage of the lead's stranded conductors during insertion procedures.

While backtwisting an unstranded conductor is typically performed, when a stranded conductor is coiled to wrap around a central core, backtwisting the stranded conductor is not necessary. This improves fatigue resistance and makes manufacturing easier. In conventional lead manufacturing procedures, unstranded conductors that are wrapped around a mandrel to form a lead are typically backtwisted. As the conductor is wrapped around a mandrel, torsion develops in the conductor that must be relieved by twisting the conductor in a direction corresponding to the developed tension. If this procedure, known as backtwisting, is not performed, the unstranded conductor will often break or cause a lead to deform because of the developed tension force.

Figure 2:
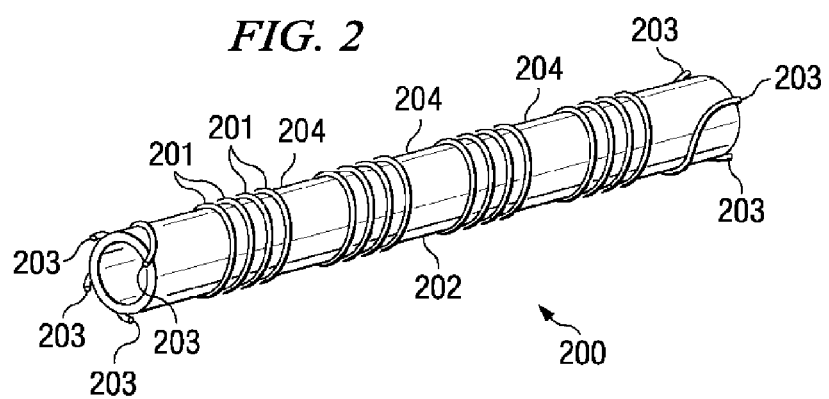
FIG. 2 shows a stranded conductor lead according to one representative embodiment.

FIG. 2 shows a lead 200 using stranded conductors according to an embodiment. Four conductors 201 are helically wound around a core 202. In other embodiments, different numbers of conductors may be used. As shown in FIG. 2, the conductors 201 are wound in groups with an inter-conductor pitch between conductors 201 within the groups. Within the groups, conductors 201 are disposed in a helical manner that is substantially normal or perpendicular to the longitudinal direction of the lead. Gaps 204 are provided between adjacent groups of conductors 201. Gaps 204 are preferably significantly larger than the inter-conductor pitch within the groups of conductors. Gaps 204 can be equal to or greater than two, three, four, or five times the inter-conductor pitch. Also, gaps 204 may be equal to or greater than one quarter of the width of an individual group of conductors, one half the width of an individual group of conductors, the width of an individual group of conductors, or twice the width of an individual group of conductors. Gaps 204 may be formed by varying the angle at which conductors 201 are wound about core 202. That is, between the helically wound groups of conductors, conductors 201 can be disposed at a largely longitudinal angle relative to the lead body. Alternatively, one or more polymer filars can be wound about core 202 in conjunction with conductors 201 to form gaps 204. The repeating pattern of conductors 201 wound in this manner enables lead 200 to elongate at relatively low stretching forces even when conductors 201 are embedded within fused insulative material. Specifically, within a lead body of fused insulative material, if conductors 201 are disposed only in a linear manner from the proximal end to the distal end of lead 200 or are only helically wound uniformly along the lead body, the lead is incapable of elongating significantly at relatively low stretching forces. It shall be appreciated that the depiction of the length of lead in FIG. 2 is shortened for the sake of clarity. A lead manufactured according to some representative embodiments would be significantly longer and possess numerous groups of conductors and intervening gaps.

At each end of lead 200, each conductor 201 terminates in a strand end 203. In the illustrated embodiment, core 202 is hollow, permitting a stiffening stylette (not shown) to be inserted through the core 202. In other embodiments, core 202 may be solid. Core 202 can be manufactured of various materials depending on the desired application. In certain embodiments, core 202 is formed from insulating material. Not shown in FIG. 2 are the insulation around each conductor 201 and insulation around the outside of lead 200.

II. Insulated Conductors

Figure 3:
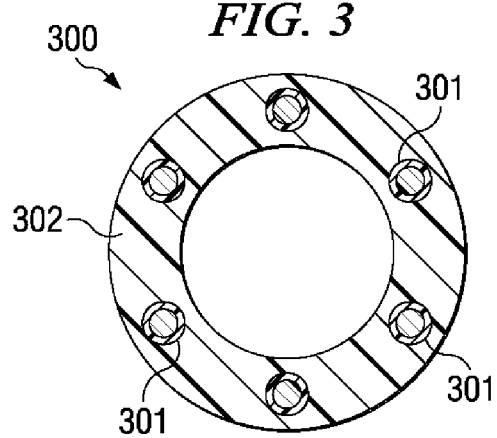
FIG. 3 shows a lead manufactured using insulated conductors according to one representative embodiment.

Referring to FIG. 3, using insulated conductors 301 provides certain benefits over the use of uninsulated conductors to form leads. Insulated conductors 301 of an embodiment comprise conductors (stranded or unstranded) coated with a very thin and tough insulating material and then used to form lead 300. In the embodiment shown in FIG. 3, a layer of insulation 302 covering lead 300 and insulated conductors 301 is used. In a preferred embodiment, the layer of insulation 302 is made of a more flexible material, such as urethane, than the insulation used to cover the individual conductors 301. In this way, the electrical isolation of the insulated conductors 301 can be maintained while retaining the flexibility of lead 300. Another advantage of using a thin insulating material to coat conductors 301 is that a small pitch (distance between adjacent conductors) provides better flexibility and durability for a lead 300 manufactured with insulated conductors 301.

III. Annealed Conductors

In some alternative embodiments, a lead body is manufactured using unstranded conductors and then cut to a desired length. This cutting process is influenced by the hardness of the conductors used to manufacture the lead. If a very hard conductor is cut, deformation forces can build up that are subsequently released when the lead is severed. In lead manufacturing, the release of deformation forces stored in a conductor can cause the component conductors of a lead to spring apart as the lead is severed.

Figure 4:
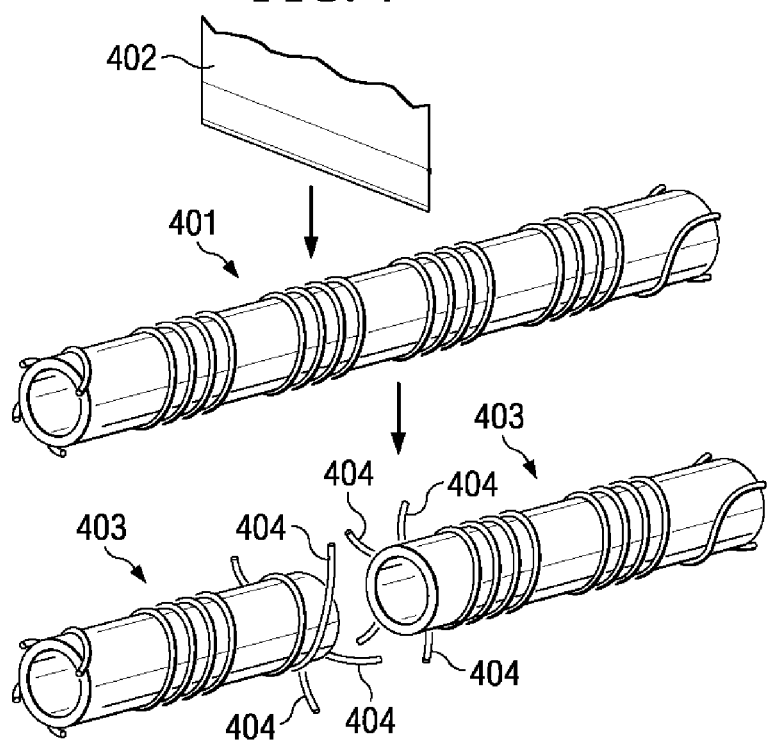
FIG. 4 shows a cut conventionally-manufactured lead.

During the lead body manufacturing process used in alternative embodiments, annealed conductors are used that are softer than their non-annealed counterparts. In general, the annealing process occurs when conductors are heated to certain temperatures in an oven and then allowed to cool, resulting in softer, more pliable material. Then, when a lead is cut, the softer annealed conductor material yields, preventing the build-up of deformation force that can cause the conductor to spring back or move during the severing process. In alternative embodiments, annealed conductors that are of reduced hardness (relative to unannealed conductors) are used to manufacture lead bodies. FIG. 4 is an illustration of what can happen when a conventionally manufactured lead is cut. Lead 401 is cut by razor 402. After the cutting process, the resulting halves 403 of lead 401 have the component conductors 404 sprung apart due to released deformation forces. Annealed conductors used in alternative embodiments can reduce or eliminate this undesirable result.

As noted above, the annealing process results in conductors that are more pliable. Generally, as described above, forming a lead from unstranded, coiled conductor requires that the conductor be backtwisted to remove torsional stresses that would otherwise contribute to the lead conductors springing apart when the lead is cut. Annealing conductors to produce pliable conductors thus can eliminate or minimize the need for backtwisting unstranded conductors to manufacture leads.

Over-annealing conductor material can result in conductors that are too soft and do not possess the mechanical integrity or robustness required for some lead applications. Accordingly, some embodiments use different degrees of annealing, so that, for example, an annealed conductor is half or a quarter as hard as unannealed conductor of the same composition. To produce annealed conductor of this type, the annealing temperature is typically reduced. For example, to produce half-hardness annealed conductor, the conductor is annealed at 500 degrees centigrade instead of 800 degrees centigrade. However, other variables in the annealing process can be modified, such as the annealing time, quenching technique (air, water, oil, etc.), quenching temperature, etc.

IV. Compliant Lead Materials

Lead materials are often chosen, particularly for implantable leads used with medical devices, to be biocompatible in composition. In many applications, a lead must also be flexible to allow for patient movement. For example, an implantable lead placed subcutaneously near an active muscle group should be capable of flexing to allow for muscle movement. Therefore, lead materials that increase lead flexibility are desirable. Additionally, when an implantable lead is implanted subcutaneously, over time the lead is encapsulated by fibrotic tissue. Fibrotic tissue is flexible, and a lead manufactured of flexible material is more compatible with the fibrotic encapsulation.

Figure 5A:
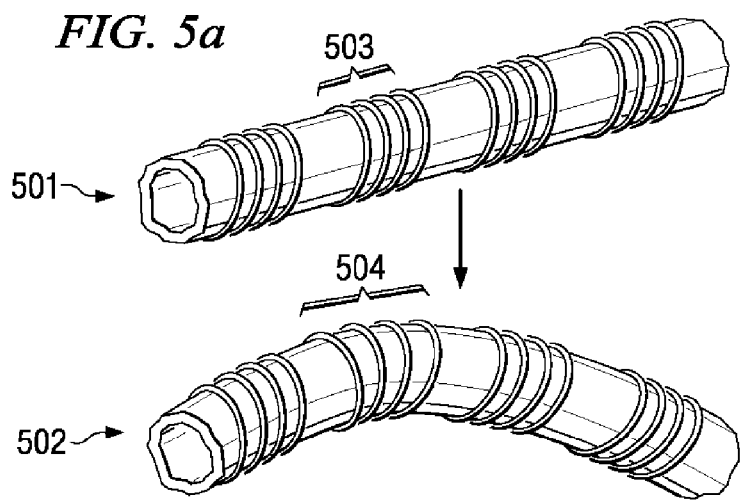
FIG. 5a illustrates conductor coils expanding or contracting as a lead manufactured according to one representative embodiment is flexed.

To manufacture a lead with desirable flexibility characteristics according to an embodiment, conductors are helically wound within a lead body of fused insulative material to permit elongation of the lead. As the lead is stretched or flexed, the conductor coils expand or contract as needed to allow the lead itself to move. An example of this coil movement is shown in FIG. 5a. An implantable lead 501 with substantially constant coiled conductor spacing 503 (within a given group of conductors along length of the lead body) has force applied, causing it to form a flexed lead 502. The coiled conductor spacing 504 has expanded on the outside of the flexed area and has contracted on the inside.

The insulative material used for fabrication of a stimulation lead is preferably selected to possess a compliant material characteristic to permit elongation of the lead. In certain embodiments, polymeric materials such as silicon rubber with elastic properties can be used to provide desired compliant or flexibility characteristics to a lead. PURASIL® and CARBOSIL® silicone-urethane copolymers are materials that can be advantageously used to fabricate leads according to some representative embodiments. Different PURASIL® or CARBOSIL® compositions, such as aromatic- and aliphatic-end-group-containing formulations, may be used in preferred embodiments. Thermal plastics comprising urethane, aromatic polyurethane, silicon, polycarbonate silicon with diol chaining, polyethers, polycarbonates, polytetrafluoroethlyene, BIONATE®, elastane, and/or other polymeric, biostable and biocompatible polymers can be also used to provide desired flexibility characteristics.

Additionally, the use of stranded conductors instead of unstranded conductors can add additional flexibility to leads, as a stranded conductor has more flexibility and also allows a certain amount of axial motion compared to an unstranded conductor which allows virtually no axial motion. Whether stranded or unstranded conductors are used, or coated or uncoated conductors, the lead coating material forms a flexible interconnection between the individual conductors of a lead. In certain embodiments, the coating material is elastic and allows the individual conductors to separate from each other or come together when the lead is flexed, while providing the requisite tension to pull the conductors back to their original positions once the lead is unflexed.

Figure 5B:
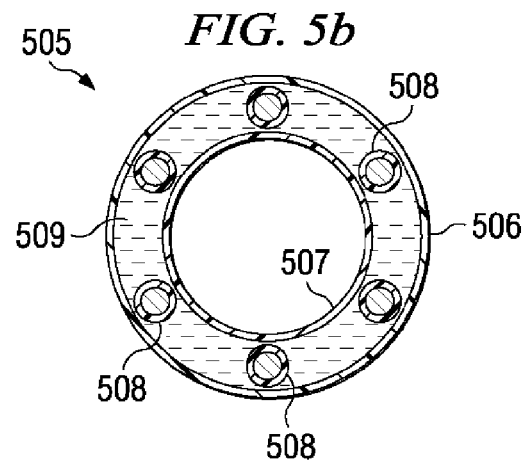
FIGS. 5b and 5c show diagrams of leads comprising inner and outer coverings around conductors.

In representative embodiments, compliant lead body materials can be used to enhance the stretching properties of a manufactured lead along the longitudinal axis. In some conventional leads where component conductors are encased in a fused insulating extrusion that also holds the conductors in place, a conventional lead does not have the ability to extend along the longitudinal axis because the component conductors are immobile. An embodiment is shown in FIG. 5b, in which lead 505 comprises a lead body of fused insulative material having an inner surface 507 and outer surface 506 with insulated conductors 508 embedded therein. Lead 505 is flexible and can stretch along the longitudinal axis of lead 505. Insulated conductors 508 are not attached or fused to the insulative material of the lead body. Conductors 508 are preferably coated with an insulating material to prevent the conductors from making electrical contact with each other. In certain alternative embodiments, a lubricating liquid or solid material 509 is inserted within lead 505. The lubricating material can prevent movement of lead 505 from causing frictional breaks in conductor insulation and/or inner surface 507 and outer surface 506. Lubricating materials such as mineral oil, coconut oil, saline solutions, cod liver oil, lecithin, etc. can be used.

In preferred embodiments, biocompatible lubricating materials are used. In certain embodiments, a relatively flexible polymer material (an intermediate polymer layer) may be disposed between inner surface 507 and outer surface 506 to encapsulate the various conductors 508. For example, conductors 508 may be coated with a relatively thin layer of perfluoroalkoxy polymer (PFA) material. The flexible polymer material can be selected to allow the various conductors 508 to be translated relative to each other and within the fused insulative material of the lead body (as would occur during lead stretching) with a minimal amount of friction.

Figure 5C:
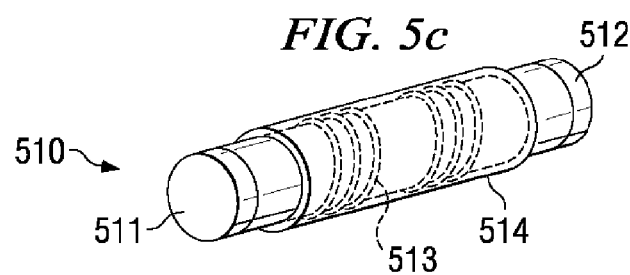

FIG. 5c shows lead 510 comprising a first end with stimulation electrode 511 and a second end comprising connector 512. Only a single electrode and connector are shown for simplicity, and other embodiments comprise more electrodes and/or connectors than shown in FIG. 5c. Stimulation electrode 511 and connector 512 are connected electrically by conductor 513. Conductor 513 can be electrically coupled to the stimulation electrode 511 and/or connector 512 using techniques described herein.

In the embodiment shown in FIG. 5c, conductor 513 is free to stretch underneath outer surface 514 as there is no connection between conductor 513 and outer surface 514. By stretching conductor 513, lead 510 can extend along a longitudinal axis, increasing the distance between stimulation electrode 511 and connector 512. This allows for a flexible and fatigue resistant lead that is body-compliant.

V. Lead Conductor Positional Control

Leads manufactured accordingly to representative embodiments may be used in a variety of applications. Use of leads in specific applications can require that a lead be of specific dimensions or diameters. Referring to FIGS. 6a and 6b, leads that are manufactured with a central lumen can have the diameter of that lumen varied depending on, for example, whether a large or small stylette is going to be inserted to stiffen the lead. Large central lumens 601 and small central lumens 602 as well as many other variations in lumen diameter can be selected to provide a central lumen appropriate for a specific application.

The distance 604 that conductors 603 are located from the inner diameter of lead 600 can also be varied by appropriate selection of a manufacturing process. In a first lead manufacturing process using a mandrel, a mandrel can first be coated with a selected amount of insulation that is extruded onto the mandrel and conductors are then wrapped onto the extruded insulation. By selecting the amount of insulation coating the mandrel, the distance 604 of a conductor from the inner diameter of the lead can thus be chosen as desired. Greater distances 604 may be desired where a stronger barrier is needed between conductors 603 and the inner lumen space for the desired application or for subsequent processing of lead 600. Greater distances 604 can also increase the fatigue life of lead 600 by preventing conductors 603 from receiving large-angle bends. A conductor's distance from both the inner and outer diameters of a lead can be controlled by varying the amount of insulation that is present on the conductor itself. Also, the distance a conductor is placed from the outer diameter of a lead can be controlled by adding an exterior coating or tubing to the lead.

Another manufacturing technique for controlling the distance 604 that conductors 603 are located from the inner diameter of lead 600 selects an extruded insulation of a desired hardness. If a very hard insulation for extrusion onto a mandrel is selected, when conductors 603 are wrapped onto the extrusion, the depth that conductors 603 penetrate into the extruded insulation is quite shallow. Conversely, if a soft insulation is selected for extrusion onto the mandrel, when conductors 603 are wrapped onto the extruded insulation, they will penetrate into the extruded insulation to a greater depth. Conductors 603 that penetrate extruded insulation to a greater depth will accordingly be located closer to the inner diameter of the lead 600 than conductors that only shallowly penetrate extruded insulation. The degree to which a conductor penetrates into extruded insulation can also be varied by changing the tension applied to the conductor as it is wrapped onto extruded insulation.

Soft extruded insulation on a mandrel can temporarily be made harder during the manufacturing process by lowering the temperature of the extrusion. Liquid nitrogen, cool gas, or other methods known to those of skill in the art can be used to lower the temperature of the extrusion and increase the hardness. In this manner, the extrusion is able to resist deformation while conductors are wrapped during the manufacturing process, yet retain flexibility once placed in service in the end application.

In certain applications, use of a hard insulation is desirable, as it provides a more solid base on which to wrap conductors and produce a consistent pitch and lay (length along the axis of a lead required for a conductor to make one complete turn around the axis) for the conductor. Consistency of the distance 605 of the conductor from the outer diameter of a lead is important when producing a lead that is resistant to dielectric breaching when placed in an application. This is because the greatest resistance to dielectric breaching is found in leads with the greatest distance 605 from a conductor to the outer diameter of a lead. Having a solid insulation base can help produce a consistent distance 605 of conductors from the outer diameter of a lead.

Also desirable in certain applications is the production of leads with short conductor pitch lengths. To maintain the smallest pitch lengths possible, conductors should be used with minimal amounts of insulation covering them. While the insulation between adjacent conductors of a lead may be sufficient to prevent the lead conductors from shorting out between each other, the insulation may be insufficient to prevent dielectric breaches between the conductors and surfaces exterior to the lead once the lead is placed in service. Therefore, certain embodiments extrude an exterior coating or place tubing over the lead conductors to prevent such dielectric breaches. In this way, a short conductor pitch length that improves fatigue resistance can be used while producing a lead that is resistant to dielectric breaches.

VI. Improved Lead Fatigue Tolerance

Conventional implantable devices use lead conductor materials such as MP35N which is a material with good corrosion resistance and good strength. In certain embodiments, low-inclusion conductor materials such as 35NLT are used to enhance the resistance of manufactured leads to fatigue-induced conductor breakage. 35NLT comprises fewer titanium inclusions. Testing indicates that leads using conductors manufactured with 35NLT are more fatigue resistant than leads using conductors manufactured with conventional MP35N. Reducing the number of material inclusions results in material with fewer sites for fracture initiation and fatigue-induced failure of the lead conductors.

VII. Lead Conductor Identification Techniques

In leads comprising more than one conductor, certain embodiments comprise methods to identify particular lead conductors to ensure that desired electrical connections are made. Conductors can be identified in certain embodiments by incorporating a dye or filler material into extruded insulation surrounding the conductor to be identified. Different dyes or filler materials can be used to identify more than one lead conductor. The conductor material itself can be dyed or oxidized in certain embodiments, using a compatible ink. Fillers used in extrusions to mark conductors are compounds, such as barium sulfate, which impart distinct color or opacity changes in the extrusions. The marking techniques used by some representative embodiments are generally selected to avoid deleterious effects to a conductor's fatigue resistance, flexibility or electrical characteristics that are present in some conventional marking techniques.

A conductor marking technique is shown in FIG. 7. In lead 700, conductor 701 is identified using a dye or filler material present in insulation extruded around conductor 701. Other conductors 702 may have different dyes or filler materials, or may remain unmarked. Conductor 701 may itself be dyed with a marking dye and then covered with an extrusion in certain embodiments. In other embodiments, conductors can alternate with a nonconductive material spacer, such as urethane, that delineates conductor groupings. While only four conductors 702 are shown in FIG. 7 and only one conductor 701 is identified, in other embodiments more conductors and more identified conductors can be used. For example, in an eight-conductor lead with each conductor numbered sequentially for identification, an identification scheme may have the number 2 conductor colored and the number 5 and 6 conductors colored.

VIII. Electrode Bonding Structures

In conventional lead designs, lead electrodes are placed onto a lead body and welded into place. In the conventional design shown in FIG. 8, lead 800 comprises a lead body 802. During manufacturing, electrode 801 with an inner diameter matching the outer diameter of lead body 802 is placed onto the lead body and welded into place. The electrode may comprise a number of electrode terminals 804 that are connected to individual conductors (not shown) from lead body 802. Because the inner diameter of electrode 801 matches the outer diameter of lead body 802, the outer diameter of the electrode protrudes above lead body 802 by a distance equal to the thickness of electrode 801, forming discontinuity 803 from lead body 802 to electrode 801. In conventional designs, such a discontinuity can be formed at the other end of the lead at, for example, where a connector is placed onto lead body 802. The discontinuity can present problems when the lead is implanted within a patient, because the discontinuity provides a location where fibrosis can more readily form. Specifically, fibrosis near electrodes 801 can significantly degrade the effectiveness of the electrical stimulation. Also, if such a lead is inserted via a needle or similar insertion apparatus, discontinuity 803 can catch on the needle or insertion apparatus. Accordingly, certain embodiments smooth the transition between lead body and any lead body connectors and/or electrodes.

In a first embodiment, a lead comprising a lead body of a first diameter and an electrode or connector of a second diameter is dipped into a liquid biocompatible material such as urethane that forms a solid covering when dried. Once dried, the covering covers the transition areas between the first and the second diameter, ensuring that the transition area is much smoother and less abrupt than the conventional design. Another advantage is that the material chosen can bond to the side of the electrode or connector facing the transition area, strengthening the electrode or connector's attachment to the lead. Any dried material covering the electrical contact area of electrodes can be laser ablated or mechanically removed from the covered surface in certain embodiments.

In a second embodiment, a lead body with an electrode and/or connector welded on is inserted into a piece of tubing of a desired biocompatible material, such as urethane. The tubing can be heat shrunk in certain embodiments to better fit the inserted lead body and fill the lead body area between connectors and/or electrodes. This will smooth the transition area between the lead body and the connectors and/or electrodes and make the transition area less abrupt. In certain embodiments, the electrodes and/or connectors can be masked off before the cover material is heat shrunk or the lead is dipped into a liquid covering material.

In either of the embodiments described above, material covering the electrode and/or connectors can be removed using mechanical cutting tools, laser ablation, or other removal tools known to those of ordinary skill in the art. Specific areas of material covering an electrode or connector can be removed, such as by laser ablation. In certain embodiments, precise techniques such as laser ablation are used to leave "dots" where the electrode or connector is exposed and can form an electrical connection. This feature allows leads to have directional electrodes or connectors in which an electrical connection can be formed in only a certain direction. Very small "dots" can be used to allow only small current flow for micro-recording or micro-electrode applications.

In yet other embodiments, a lead body without attached electrodes can be dipped in a liquid biocompatible material such as urethane that forms a solid covering when dried. After the material has dried, the proximal and distal ends of the lead body can have the solid covering removed by ablation or mechanical means and electrodes then attached. A laser can then be used to weld the electrodes to the correct conductors in the lead body.

The dipping process described above can also be used to form a rounded tip of the biocompatible material at the distal end of an electrode. This tip can be useful when the lead is inserted during an installation procedure to prevent trauma to tissue as the biocompatible material is typically softer than the other lead materials. Also, for leads that comprise an inner lumen for stylette insertion, the tip can form a positive stop for an inserted stylette.

IX. Lead Anchor Systems

A lead that is implanted in tissue will, over time, induce the surrounding tissue to encapsulate the lead. Leads with a rough surface can encourage such encapsulation and provide anchor points to prevent movement of the lead using the encapsulating tissue. Certain embodiments can regulate the amount of roughness on the exterior of a manufactured lead thereby controlling the strength of the lead's encapsulation. For example, a lead that is temporarily implanted would have a smoother surface to aid in the eventual removal of the lead, while a permanently-implanted lead would have a rougher surface, particularly if implanted at a location that will subject the lead to movement or dislocation forces.

Figure 9A:
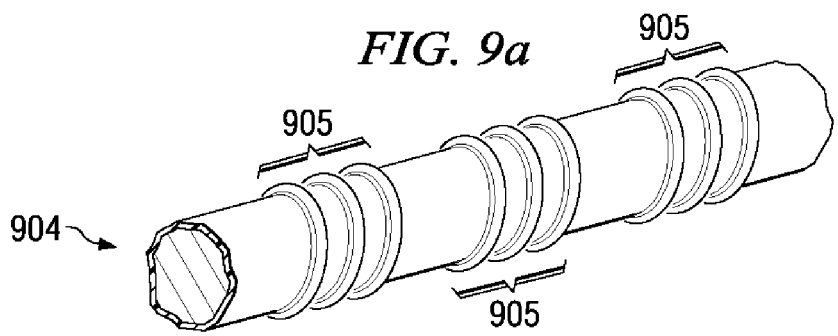
FIGS. 9a and 9b show leads with surface textures controlled during manufacturing according to some representative embodiments.

Certain embodiments provide a rough exterior lead surface by forming a lead from conductors that are insulation-coated. The conductors are then wrapped around a central tube or rod. Finally, the conductors are heated using a heat source, such as a laser, and partially melted so that the insulation of adjacent conductors merges without causing a short between the conductors. The resulting exterior lead surface will have a ribbed or marbled texture that is suitable for encouraging tissue encapsulation. FIG. 9a shows such a lead 904 with ribs 905 formed by the conductors.

In other embodiments, the exterior surface of the lead can be roughened using a laser or mechanical system to form tiny fibers or holes in the surface. Tissue can then surround the fibers or grow into the holes, assisting with anchoring the lead. Additionally, lead tips can be formed, again using lasers or mechanical means, so that the tip has a valley or hole that tissue can grow into thereby anchoring the lead.

Figure 9B:
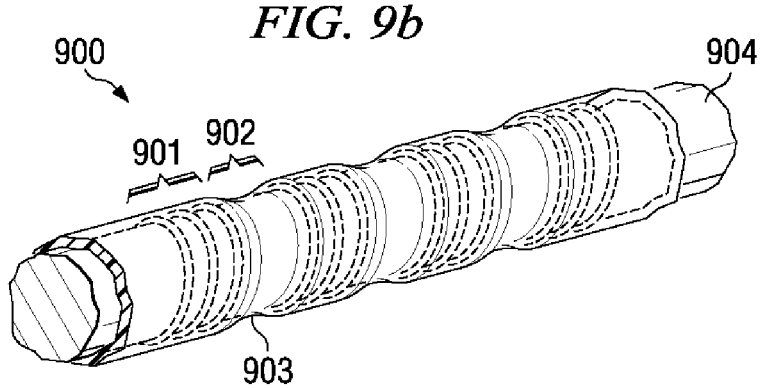

In yet other embodiments, conductors can be wrapped with a space between groups of conductors. In the example shown in FIG. 9b, lead 900 comprises a set of three conductors 901 that are wound around central rod 904 with gap 902 in the conductor spacing. The gap results in a depression 903 on the exterior surface of the lead for tissue to grow into. In some embodiments, a filler material as described above can be placed into a gap between conductors. The filler material can then be excised during installation of the lead as determined by a medical professional or other person. The region formed by the excise of filler material can then be utilized with a suture or allowed to remain free to become encapsulated by surrounding tissue.

In certain embodiments, anchor material can be attached to a lead via sutures, welding, or other means known to those of skill in the art.

Although certain representative embodiments have been discussed in terms of spinal cord stimulation systems, it shall be appreciated that stimulation leads having compliant material characteristics could be employed for any suitable stimulation therapy. For example, some embodiments could employ compliant stimulation leads for cortical stimulation, gastric pacing stimulation, sacral or pudendal nerve stimulation, cranial nerve stimulation, cardiac stimulation for pacing, defibrillation, etc., functional muscle stimulation, etc.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

What is claimed is:

1. A method of fabricating a neurostimulation lead adapted for electrical stimulation of tissue of a patient, comprising:

forming a lead body of insulative material, the insulative material being fused through a substantial volume of the lead body and along a substantial length of the lead body, wherein (i) a plurality of conductors are embedded within the insulative material, (ii) the plurality of conductors are disposed in a helical manner in a repeating pattern of groups of conductors separated by gaps along a substantial length of the lead body, each gap being larger than an inter-conductor pitch within the groups of conductors, (iii) the insulative material is a compliant polymer material, wherein after being formed, the lead body is adapted to permit repetitive elastic axial elongation, without damaging the plurality of conductors, along a majority of the length of the lead body at low stretching forces on the lead body imposed by posture changes of the torso of the patient after implant within the patient's body, and (iv) the lead body assumes a generally linear configuration when a stretching force is not applied to the lead body;

creating a plurality of electrodes on a distal end of the lead body; and creating a plurality of terminals on a proximal end of the lead body, wherein the plurality of electrodes are electrically coupled to the plurality of terminals through the plurality of conductors.

2. The method of claim 1 wherein the forming comprises:
   subjecting the lead body to heat and pressure to fuse the compliant insulative material coating the plurality of conductors with other insulative material of the lead body.

3. The method of claim 1 wherein the forming comprises:
   winding the plurality of conductors around an inner insulative layer or a mandrel by repetitively varying an angle to which the plurality of conductors are disposed relative to the inner insulative layer or mandrel to form the groups and the gaps between the groups along a substantial length of the lead body.

4. The method of claim 1 wherein the forming comprises:
   fusing one or more elastic filars to other insulative material of the lead body to define the gaps between the groups of conductors.

5. The method of claim 1 wherein the gaps are greater than two times the inter-conductor pitch within the groups of conductors.

6. The method of claim 1 wherein the plurality of conductors are stranded wire conductors.

7. The method of claim 1 wherein the insulative material of the lead body is substantially composed of a silicone urethane copolymer material.

8. The method of claim 1 wherein the lead body stretches at least 25% when a stretching force of less than 3 lbs is applied to the lead.

9. The method of claim 1 wherein the lead body stretches at least 25% when a stretching force of less than 1 lb is applied to the lead.

* * * * *